(12) United States Patent
Bowen et al.

(10) Patent No.: US 11,529,363 B2
(45) Date of Patent: Dec. 20, 2022

(54) METHODS OF TREATING CANCER IN PEDIATRIC PATIENTS

(71) Applicant: ARIAD Pharmaceuticals, Inc., Cambridge, MA (US)

(72) Inventors: Sharon Bowen, Cambridge, MA (US); Michael Hanley, Cambridge, MA (US); David Kerstein, Cambridge, MA (US); Karthik Venkatakrishnan, Cambridge, MA (US)

(73) Assignee: TAKEDA PHARMACEUTICAL COMPANY LIMITED

( * ) Notice: Subject to any disclaimer, the term of this patent is extended or adjusted under 35 U.S.C. 154(b) by 117 days.

(21) Appl. No.: 16/982,378

(22) PCT Filed: Mar. 18, 2019

(86) PCT No.: PCT/US2019/022674
§ 371 (c)(1),
(2) Date: Sep. 18, 2020

(87) PCT Pub. No.: WO2019/182936
PCT Pub. Date: Sep. 26, 2019

(65) Prior Publication Data
US 2021/0000845 A1    Jan. 7, 2021

Related U.S. Application Data

(60) Provisional application No. 62/645,089, filed on Mar. 19, 2018.

(51) Int. Cl.
| | | |
|---|---|---|
| *A61K 31/675* | (2006.01) | |
| *A61P 35/04* | (2006.01) | |
| *A61K 9/00* | (2006.01) | |
| *A61K 31/519* | (2006.01) | |
| *A61K 31/573* | (2006.01) | |
| *A61K 31/704* | (2006.01) | |
| *A61K 31/7048* | (2006.01) | |
| *A61K 31/7068* | (2006.01) | |
| *A61K 45/06* | (2006.01) | |

(52) U.S. Cl.
CPC ............ *A61K 31/675* (2013.01); *A61P 35/04* (2018.01); *A61K 9/0053* (2013.01); *A61K 31/519* (2013.01); *A61K 31/573* (2013.01); *A61K 31/704* (2013.01); *A61K 31/7048* (2013.01); *A61K 31/7068* (2013.01); *A61K 45/06* (2013.01)

(58) Field of Classification Search
CPC .............................. A61K 31/675; A61P 35/00
See application file for complete search history.

(56) References Cited

U.S. PATENT DOCUMENTS

2021/0186994 A1*  6/2021  Verwijs ................ A61K 31/662

FOREIGN PATENT DOCUMENTS

| WO | 2015/066452 A2 | 5/2015 |
| WO | 2015/097621 A2 | 7/2015 |
| WO | 2016/065028 A1 | 4/2016 |

OTHER PUBLICATIONS

Renato et al. Blood, 1996, 84(7):1243-8.*
Brugieres, L., et al, "Anaplastic large cell lymphoma (ALCL) in children: Equal efficacy but greater toxicity of chemotherapy including methotrexate (MTX) 1 g/m(2) in 24 hour infusion with intrathecal injection (IT) than chemotherapy with MTX 3 g/m(2) in 3 hours infusion without IT: Results of the ALCL99-R1 randomised Trial", Blood; American Society of Hematology, US; vol. 108, No. 11, Part 1, Nov. 16, 2006 (Nov. 16, 2006), p. 122A.
Eyre, T. et al, "Anaplastic lymphoma kinase-positive anaplastic large cell lymphoma: current and future perspectives in adult and paediatric disease", European Journal of Haematology, Munskgaard, Copenhagen, DK, vol. 93, No. 6, Nov. 30, 2014 (Nov. 30, 2014), pp. 455-468.
Huang, Wei-Sheng et al, "Discovery of AP26113, a potent, orally active inhibitor of anaplastic lymphoma kinase and clinically relevant mutants", Cancer Research, vol. 75, No. Suppl. 15, Aug. 2015 (Aug. 2015), p. 2827.
Lowe E J et al: "Potential therapies for anaplastic lymphoma kinase-driven tumors in children: Progress to date", Paediatric Drugs, ADIS International, Auckland, NZ, vol. 15, No. 3, May 31, 2013 (May 31, 2013), pp. 163-169.

* cited by examiner

*Primary Examiner* — Rei Tsang Shiao
(74) *Attorney, Agent, or Firm* — Honigman LLP; Andrew S. Chipouras; Jonathan P. O'Brien

(57) ABSTRACT

Provided herein are methods for treating cancers (e.g., inflammatory myofibroblastic tumor, anaplastic large cell lymphoma, and neuroblastoma) in pediatric patients using brigatinib, as monotherapy or combination therapy with one or more second therapeutic agents.

36 Claims, 3 Drawing Sheets

METHODS OF TREATING CANCER IN PEDIATRIC PATIENTS

CROSS-REFERENCES TO RELATED APPLICATIONS

This application is a 35 U.S.C. § 371 U.S. National Phase Application of, and claims priority to, PCT Application No. PCT/US2019/022674, filed Mar. 18, 2019, which claims priority to U.S. Provisional Application No. 62/645,089, filed Mar. 19, 2018, the entirety of which is incorporated herein by reference.

FIELD

Provided herein are methods for treating cancers (e.g., inflammatory myofibroblastic tumor and anaplastic large cell lymphoma) in pediatric patients using brigatinib, as monotherapy or combination therapy with one or more second therapeutic agents.

BACKGROUND

Brigatinib is a novel, orally (PO) administered tyrosine kinase inhibitor (TKI). Brigatinib potently inhibits activated variants of anaplastic lymphoma kinase (ALK).

ALK is a tyrosine kinase encoded on chromosome 2 that performs a physiologic role in early brain development. Expression levels are low in adults; however, ALK can be altered and become active in several malignancies, including non-small cell lung cancer (NSCLC), an adult disease, as well as inflammatory myofibroblastic tumor (IMT) and anaplastic large cell lymphoma (ALCL), which predominantly afflict pediatric patients or young adults. In each of these conditions, the most frequent ALK alterations involve formation of fusion genes due to chromosomal rearrangements. Holla et al., *Cold Spring Harb. Mol. Case Stud.* 2017, 3(1), a001115. The first genetic rearrangement of ALK discovered in NSCLC involved a fusion between the echinoderm microtubule-associated protein-like 4 (EML4) gene and the ALK tyrosine kinase domain (KD). Since then, a number of additional ALK fusion partners have been described that are believed to result in aberrant signaling and oncogenic transformation. Rikova et al., *Cell* 2007, 131(6), 1190-203; Takeuchi et al., *Clin. Cancer Res.* 2009, 15(9), 3143-9. In contrast to fusion genes seen in NSCLC, IMT, and ALCL, activating mutations of full-length ALK without rearrangement occur in neuroblastoma, another predominantly pediatric cancer. Holla et al., 2017.

Three ALK inhibitors, crizotinib, ceritinib, and alectinib, are approved in Europe for treatment of patients with advanced anaplastic lymphoma kinase positive (ALK+) NSCLC. Additionally, brigatinib has received accelerated approval by the United States Food and Drug Administration (FDA) for treatment of ALK+ metastatic NSCLC among patients who have progressed on or are intolerant to crizotinib, and the European Marketing Authorisation Application (MAA) for use of brigatinib in the treatment of ALK+ NSCLC patients with prior crizotinib treatment is under review. While the ALK inhibitor crizotinib is an effective treatment for ALK+ NSCLC, 26% to 35% of patients fail to respond, and the majority progress within 1 year. Ultimately, ALK-dependent mechanisms of resistance are observed in approximately 30% of NSCLC patients treated with crizotinib due mainly to acquisition of secondary mutations in the ALK fusion gene that interfere with crizotinib binding and/or amplification. Gainor et al., *Clin. Cancer Res.* 2013, 19(15), 4273-81; Katayama et al., *Clin. Cancer Res.* 2015, 21(10), 2227-35; Toyokawa et al., *J. Thorac. Oncol.* 2015, 10(7), e55-7. Importantly, newer agents, including brigatinib, have demonstrated the capacity to overcome many of these resistance mechanisms. Zhang et al., *Clin. Cancer Res.* 2016, 22(22), 5527-38. In in vitro studies, brigatinib was a more potent ALK inhibitor than crizotinib, ceritinib, and alectinib, and is the only of these agents to maintain substantial activity against all 17 secondary ALK mutants of EML4-ALK tested at relevant levels of exposure achieved in patients.

In addition to promising nonclinical findings, brigatinib demonstrated substantial systemic and intracranial responses in a first-in-human (FIH) study (Study AP26113-11-101) and a phase 2 study (Study AP26113-13-201; the ALTA trial) among adult patients with ALK+ NSCLC who were refractory to crizotinib. In ALTA, robust objective response rates (ORR) and durability of response were observed with a 180 mg daily dose, which was initiated following a 7-day lead-in with 90 mg daily (90→180 mg once daily (QD)). In this study, the investigator-assessed confirmed ORR, duration of response (DOR), and progression-free survival (PFS) at the 90→180 mg QD dose were 55.5% and 13.8 and 15.6 months, respectively. A phase 3 trial (Study AP26113-13-301; ALTA 1L) is underway with a primary objective of comparing the efficacy of brigatinib to crizotinib based on PFS in patients with ALK+ locally advanced or metastatic NSCLC who are naive to ALK inhibitor treatment.

NSCLC is principally an adult disease, as cases are extremely rare among children and adolescents. However, as previously mentioned, ALK is rearranged, mutated, or amplified in a variety of tumors relevant to the pediatric population, including IMT, ALCL, and neuroblastoma. Therefore, ALK remains a rational therapeutic target for pediatric patients with these conditions. Takita, *Cancer Sci.* 2017, 108(10), 1913-20.

The first of these cancers, IMT, is a very rare solid tumor characterized by spindle-shaped myofibroblastic cells with a chronic inflammatory component that mostly occurs in children and adolescents, primarily in the lung, soft tissues, and the abdominal region. Chromosomal translocations leading to ALK activation are present in 50% to 70% of IMTs, and are more common at younger ages; the most common are tropomyosin 3/4 (TPM3/4)-ALK fusions, but, as in NSCLC, EML4-ALK inversions are also seen. Alaggio et al., *Cancer* 2009, 116(1), 216-26; Griffin et al., *Cancer Res.* 1999, 59(12), 2776-80; Antonescu et al., *Am. J. Surg. Pathol.* 2015, 39(7), 957-67. IMT treatment is generally limited to surgical resection, and there are no standard pharmacologic approaches for advanced/recurrent disease or when complete resection is not possible. Dalton et al., *J. Pediatr. Surg.* 2016, 51(4), 541-4.

The second of these conditions, ALCL, is a rare (~110 new cases/year in Europe) form of non-Hodgkin lymphoma (NHL) that also occurs predominantly in children and adolescents. It is characterized by proliferation of lymphoid T cells or null cells that express CD30. Up to 90% of pediatric ALCL patients have ALK+ disease, whereas adult ALCL patients exhibit ALK positivity less frequently (50%). Damm-Welk et al., *Blood* 2007, 110(2), 670-7; Gustafson et al., *Ann. Diagn. Pathol.* 2009, 13(6), 413-27. Translocations involving nucleophosmin 1 (NPM1)-ALK and TPM3-ALK fusions account for 75% to 80% and 12% to 18%, respectively, of ALK+ ALCL. Holla et al., 2017; Pulford et al., *J. Cell Physiol.* 2004, 199(3), 330-58. ALCL is very chemosensitive and several chemotherapy regimens have been utilized in both the front-line and refractory settings.

Lastly, neuroblastoma is a rare (<100 new ALK+ cases/year in Europe) childhood malignancy arising from the embryonic sympathetic nervous system. As opposed to IMT and ALCL, where ALK translocations predominate, activating point mutations of ALK are important drivers of oncogenesis in neuroblastoma, with ALK mutations present in nearly all cases of familial neuroblastoma and between 6% and 10% of spontaneous disease. Louis et al., *Annu. Rev. Med.* 2015, 66, 49-63; Mosse et al., *Nature* 2008, 455(7215), 930-5. Other significant driver oncogenes are well established in neuroblastoma, with the most prominent being amplification of MYCN. Standard treatments of neuroblastoma involve chemotherapy, resection, radiotherapy, biologic treatments, and immunotherapy, depending on risk status. Berlanga et al., *Expert Opin. Emerg. Drugs* 2017, 22(1), 63-75.

With respect to IMT, there are no approved or rigorously studied pharmacologic approaches to managing this condition. As such, patients who are ineligible for resection due to complex lesions or other factors represent the highest unmet need of the IMT patient population. Therefore, novel agents that can control unresectable lesions or serve as neoadjuvant therapy to enable resection are needed and would represent a major advance for these patients.

Today, most European pediatric groups utilize the ALCL99 chemotherapy regimen as standard therapy for ALCL. This approach is derived from the BFM protocol previously used in aggressive B-cell NHL. Treatment regimens differ somewhat across studies but typically involve cyclophosphamide, doxorubicin, vincristine, corticosteroids, ifosfamide, and etoposide given for 4 to 6 months, with high-dose methotrexate and cytarabine for central nervous system (CNS) prophylaxis. Eyre et al., *European Journal of Haematology* 2014, 93(6), 455-68; Turner et al., *Br. J. Haematol.* 2016, 173(4), 560-72. The EFS rate observed in the largest of the ALCL99-based studies completed to date was 73% at 2 years. After initial therapy, approximately 20% to 40% of patients with ALCL subsequently develop recurrent disease. Patients at highest risk for recurrence appear to be those with MDD+ status and anti-ALK antibody titers ≤1/750. Mussolin et al., *Leukemia* 2013, 27(2), 416-22. Nevertheless, a main objective of ongoing research must include identifying treatment regimens that prevent recurrence in patients with known high-risk ALCL, and there is a high unmet need for better therapies for these patients. Accordingly, ALCL patients who exhibit high-risk traits (e.g., MDD at diagnosis or low ALK antibody titers) may benefit from more aggressive or diverse front-line interventions that drive deeper response, with the objective of preventing or forestalling recurrence, particularly since recurrence is associated with poor prognosis.

SUMMARY

Provided herein are methods for treating a cancer in a pediatric patient having the cancer, comprising administering to the patient a therapeutically effective amount of Compound A of the formula:

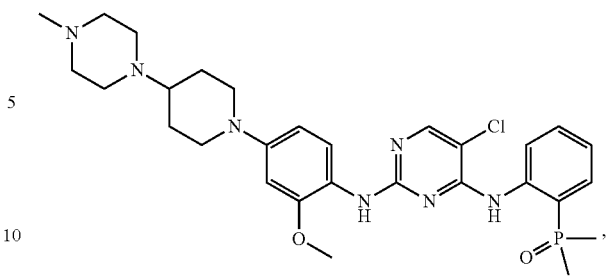

or a pharmaceutically acceptable salt thereof. Compound A can be administered as a monotherapy or in a combination therapy with one or more second therapeutic agents.

In one embodiment, the cancer is inflammatory myofibroblastic tumor (IMT), anaplastic large cell lymphoma (ALCL), or neuroblastoma. In one embodiment, the cancer is inflammatory myofibroblastic tumor (IMT) or anaplastic large cell lymphoma (ALCL).

Also provided herein are pharmaceutical compositions, dosage forms, dosing regimens, and kits that can be used in connection with the above-described methods.

DETAILED DESCRIPTION

Definitions

Figure 1:
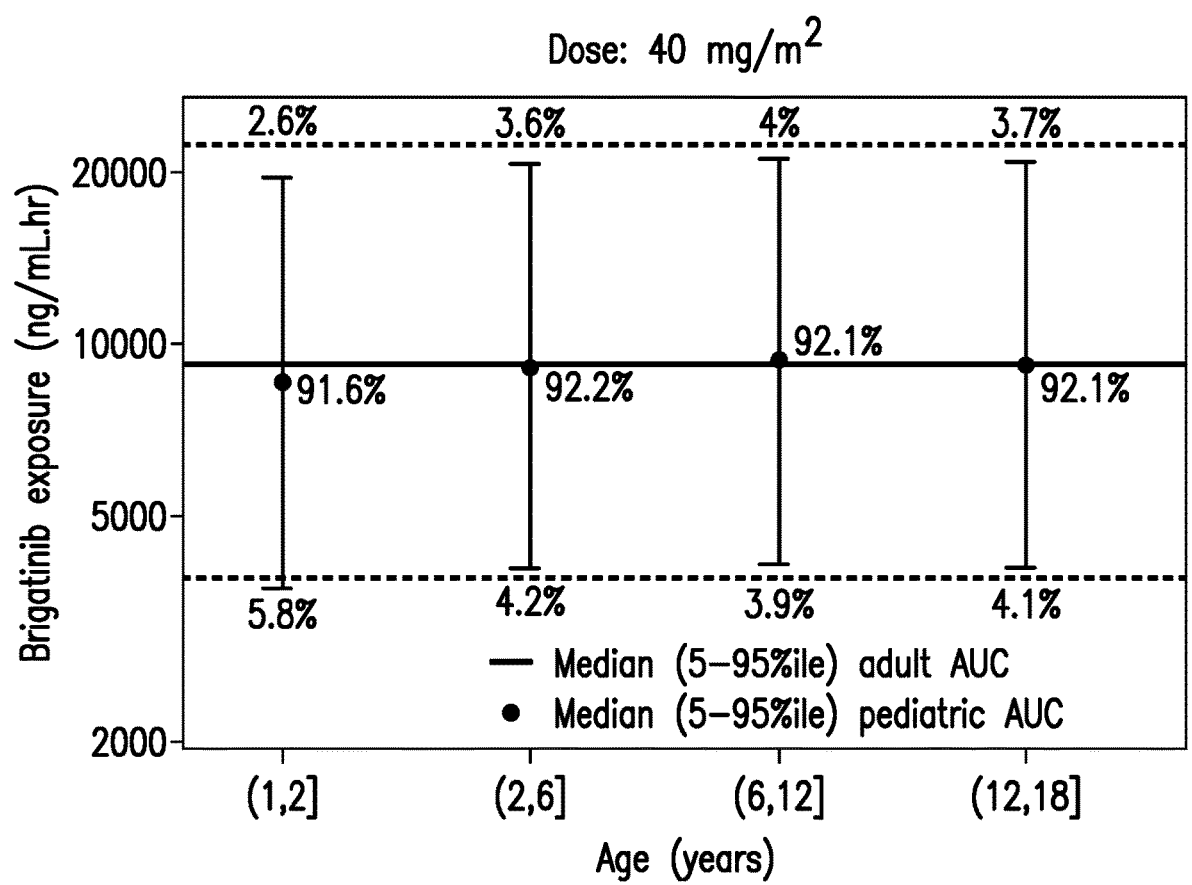
FIG. 1 shows comparison of simulated brigatinib systemic exposures (AUC) in pediatric patients receiving 40 mg/m$^2$ of the oral solution versus adult patients receiving 90 mg of the oral tablet.

Unless defined otherwise, all technical and scientific terms used herein have the same meaning as is commonly understood by one of skill in the art to which this disclosure belongs. All patents, applications, published applications and other publications referred to herein are incorporated by reference in their entirety. Headings used herein are for organizational purposes only and in no way limit the invention described herein.

As used herein and unless otherwise specified, the term "administer" or "administration" refers to the act of physically delivering a substance as it exists outside the body into a patient, such as by oral, mucosal, intradermal, intravenous, intramuscular delivery and/or any other method of physical delivery described herein or known in the art. When a disease, disorder or condition, or a symptom thereof, is being treated, administration of the substance typically occurs after the onset of disease, disorder or condition or symptoms thereof. When a disease, disorder or condition, or symptoms thereof, are being prevented, administration of the substance typically occurs before the onset of the disease, disorder or condition or symptoms thereof.

As used herein and unless otherwise specified, the terms "treatment," "treat," and "treating" are meant to include the full spectrum of intervention for a disease, disorder or condition from which the subject is suffering, such as to alleviate, slow, stop, or reverse one or more symptoms of the disease, disorder or condition or to delay the progression of the disease, disorder or condition even if the disease, disorder or condition is not actually eliminated. Treatment can include, e.g., a decrease in the severity of a symptom, the number of symptoms, and/or frequency of relapse. Treatment of a cancer can include, e.g., inhibition of tumor growth, arrest of tumor growth, and/or regression of already existing tumors.

As used herein and unless otherwise specified, the terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

As used herein and unless otherwise specified, the terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

As used herein and unless otherwise specified, the terms "cancer" and "cancerous" refer to or describe the physiological condition in mammals that is typically characterized by unregulated cell growth.

As used herein and unless otherwise specified, the terms "tumor" and "solid tumor" as used herein, refer to all lesions and neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein and unless otherwise specified, the terms "subject" and "patient" are used interchangeably. As used herein, a subject can be a mammal such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a disease, disorder or condition described herein. In another embodiment, the subject is a mammal (e.g., a human) at risk of developing a disease, disorder or condition described herein.

As used herein and unless otherwise specified, the term "effective amount" or "therapeutically effective amount" refers to that the amount of a compound, or combination of one or more compounds when administered (e.g., sequentially or simultaneously) that elicits the desired biological or medicinal response, e.g., destroys the target cancer cells or slows or arrests the progression of the cancer in a subject. The therapeutically effective amount may vary depending upon the intended application (in vitro or in vivo), or the subject and disease condition being treated, e.g., the weight and age of the subject, the severity of the disease condition, the manner of administration and the like, which can readily be determined by one skilled in the art. The term also applies to a dose that induces a particular response in target cells, e.g., reduction of platelet adhesion and/or cell migration. For example, the "therapeutically effective amount" of a combination therapy refers to the amounts of each therapeutic agent of the combination therapy that, when administered in combination, have a beneficial effect. In certain embodiments, the combined effect is additive. In certain embodiments, the combined effect is synergistic. Further, it is to be recognized by one skilled in the art that in the case of combination therapy, the amount of each therapeutic agent may independently be used in a "sub-therapeutic amount", i.e., less than the therapeutically effective amount of the therapeutic agent alone.

As used herein and unless otherwise specified, the term a "sub-therapeutic amount" of an agent or therapy is an amount less than the effective amount for that agent or therapy as a single agent, but when combined with an effective or sub-therapeutic amount of another agent or therapy can produce a result desired by the physician, due to, for example, synergy in the resulting efficacious effects, or reduced side effects.

As used herein and unless otherwise specified, combination therapy or "in combination with" refer to the use of more than one therapeutic agent to treat a particular disorder or condition. By "in combination with," it is not intended to imply that the therapeutic agents must be administered at the same time and/or formulated for delivery together, although these methods of delivery are within the scope of this disclosure. A therapeutic agent can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other additional agents. The therapeutic agents in a combination therapy can also be administered on an alternating dosing schedule, with or without a resting period (e.g., no therapeutic agent is administered on certain days of the schedule). The administration of a therapeutic agent "in combination with" another therapeutic agent includes, but is not limited to, sequential administration and concomitant administration of the two agents. In general, each therapeutic agent is administered at a dose and/or on a time schedule determined for that particular agent. Higher combinations, e.g., triple therapy, are also contemplated herein.

As used herein and unless otherwise specified, the term "concomitant administration" or "co-administration" refers to that two or more therapeutic agents are administered to the same subject at the same time (simultaneously) or at about the same time. "At about the same time" encompasses sequential administration where the period between administrations is due only to the speed of the individual administering the active agents, rather than an intentional period of delay between administrations, e.g., the time period necessary for a single health care practitioner to administer a first therapeutic agent according to accepted clinical practices and standards, and then administer a second therapeutic agent according to accepted clinical practices and standards. In one embodiment, "at about the same time" encompasses administrations within a time period of fifteen minutes or less, thirty minutes or less, one hour or less, two hours or less, six hours or less, up to about twelve hours or less. In one embodiment, concomitant administration occurs in a time period of no more than about fifteen minutes, no more than about thirty minutes, no more than about one hour, no more than about two hours, or no more than about six hours, and does not extend beyond 12 hours.

As used herein and unless otherwise specified, the term "sequential administration" refers to administration of at least two therapeutic agents at different times, the administration route being identical or different. In a particular embodiment of sequential administration, the administration of one of the therapeutic agents is completed before administration of the other or others commences. The delay between the administration of different therapeutic agents may be intentional, e.g., for the purpose of achieving certain beneficial therapeutic effects. In one embodiment, sequential administrations occurs in a time separation of no less than about thirty minutes, no less than about one hour, no less than about two hours, no less than about six hours, no less than about twelve hours, or no less than about 24 hours. In one embodiment, sequential administrations occurs in a time separation of no less than about 1 day, about 2 days, about 3 days, about 4 days, about 5 days, about 6 days, about 7 days, or even longer. In one embodiment, sequential administrations occurs in a time separation of no less than 12 hours.

As used herein and unless otherwise specified, the term "synergistic effect" refers to a situation where the combination of two or more agents produces a greater effect than the sum of the effects of each of the individual agents. The term encompasses not only a reduction in symptoms of the disorder to be treated, but also, e.g., an improved side effect profile, improved tolerability, improved patient compliance, improved efficacy, or any other improved clinical outcome.

As used herein and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein and unless otherwise specified, the term "pharmaceutically acceptable salt" refers to salts derived from a variety of organic and inorganic counter ions well known in the art. Pharmaceutically acceptable acid addition salts may be formed with inorganic acids and organic acids. For reviews of suitable salts, see, e.g., BERGE et al., J. Pharm. Sci. 66:1-19 (1977) and Remington: The Science and Practice of Pharmacy, 20th Ed., A. Gennaro, Lippincott Williams & Wilkins, 2000. Non-limiting examples of suitable acid salts includes: hydrochloric acid, hydrobromic acid, sulfuric acid, nitric acid, phosphoric acid, acetic acid, propionic acid, glycolic acid, pyruvic acid, oxalic acid, maleic acid, malonic acid, succinic acid, lactate acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Non-limiting examples of suitable base salts includes: sodium, potassium, lithium, ammonium, calcium, magnesium, iron, zinc, copper, manganese, aluminum, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

As used herein and unless otherwise specified, the term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the disclosure is contemplated. Supplementary active ingredients can also be incorporated into the compositions.

As used herein and unless otherwise specified, the terms "carrier", "adjuvant", or "vehicle" are used interchangeably herein, and include any and all solvents, diluents, and other liquid vehicles, dispersion or suspension aids, surface active agents, isotonic agents, thickening or emulsifying agents, preservatives, solid binders, lubricants and the like, as suited to the particular dosage form desired. Remington: The Science and Practice of Pharmacy, 20th Ed., A. Gennaro, Lippincott Williams & Wilkins, 2000 discloses various carriers used in formulating pharmaceutically acceptable compositions and known techniques for the preparation thereof. Except insofar as any conventional carrier medium is incompatible with the compounds of the disclosure, such as by producing any undesirable biological effect or otherwise interacting in a deleterious manner with any other component(s) of the pharmaceutically acceptable composition, its use is contemplated to be within the scope of this disclosure.

Unless otherwise stated, compounds described herein include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the disclosure.

Unless otherwise stated, compounds described herein include all stereochemical forms of the structure, e.g., the R and S configurations for each asymmetric center. Therefore, single stereochemical isomers as well as enantiomeric and diastereomeric mixtures of the present compounds are within the scope of the disclosure. In the compounds described herein where relative stereochemistry is defined, the diastereomeric purity of such a compound may be at least 80%, at least 90%, at least 95%, or at least 99%. As used herein, the term "diastereomeric purity" refers to the amount of a compound having the depicted relative stereochemistry, expressed as a percentage of the total amount of all diastereomers present.

Methods of Treatment

In one embodiment, provided herein is a method for treating a cancer in a pediatric patient having the cancer, comprising administering to the patient a therapeutically effective amount of Compound A of the formula:

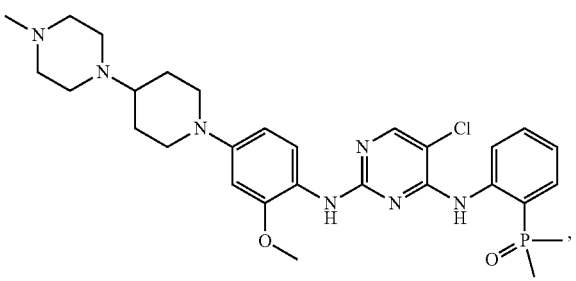

or a pharmaceutically acceptable salt thereof.

In one embodiment, provided herein is a method for preventing a cancer in a pediatric patient, comprising administering to the patient a therapeutically effective amount of Compound A or a pharmaceutically acceptable salt thereof.

Compound A is also known as brigatinib, and has a chemical name of 5-chloro-N4-[2-(dimethylphosphoryl)phenyl]-N2-{2-methoxy-4-[4-(4-methylpiperazin-1-yl)piperidin-1-yl]phenyl}pyrimidine-2,4-diamine. Brigatinib is described in WO 2009/143389, which is incorporated herein by reference. Example 122 of WO 2009/143389 describes the synthesis of brigatinib. Several polymorphic forms of brigatinib are described in WO 2016/065028, which is incorporated herein by reference.

Compound A, or a pharmaceutically acceptable salt thereof, can be administered as a monotherapy or in a combination therapy with one or more second therapeutic agents.

In one embodiment, the patient is <22 years of age. In one embodiment, the patient is ≤18 years of age. In one embodiment, the patient is ≥1 and <22 years of age. In one embodiment, the patient is ≥1 and ≤18 years of age. In one embodiment, the patient is 1 to 17 years of age. In one embodiment, the patient is ≥2 and <22 years of age. In one embodiment, the patient is ≥2 and ≤18 years of age. In one embodiment, the patient is 2 to 17 years of age. In one embodiment, the patient is ≥4 and <22 years of age. In one embodiment, the patient is ≥4 and ≤18 years of age. In one embodiment, the patient is 4 to 17 years of age.

In one embodiment, the cancer is anaplastic lymphoma kinase positive (ALK+). As used herein and unless otherwise specified, an "ALK positive" (ALK+) cancer refers to a cancer characterized by inappropriately high expression of an ALK gene, or the presence of a mutation in an ALK gene that alters the biological activity of an ALK nucleic acid molecule or polypeptide. As used herein and unless otherwise specified, a "mutation" or "mutant" of ALK comprises one or more deletions, substitutions, or additions in the amino acid or nucleotide sequences of ALK, or fragments thereof. ALK mutants also include ALK fusion proteins and ALK fusion genes. The ALK mutant can also include one or more deletions, substitutions, or additions, or a fragment thereof, as long as the mutant retains kinase phosphorylation activity. In one embodiment, the ALK mutant is EML4-ALK, a fusion between the echinoderm microtubule-associated protein-like 4 (EML4) gene and the ALK tyrosine kinase domain, including any secondary mutant of EML4-ALK such as those described in U.S. Pat. No. 9,611,283, the entirety of which is incorporated herein by reference.

In one embodiment, the ALK+ cancer is determined by an FDA-approved test or other tests known in the art. The tests that can be used include, e.g., FoundationOne CDx™ (F1CDx) (a sequencing based in vitro diagnostic device for detection of substitutions, insertion and deletion alterations (indels), and copy number alterations (CNAs) in 324 genes and select gene rearrangements, as well as genomic signatures including microsatellite instability (MSI) and tumor mutational burden (TMB) using DNA isolated from formalin-fixed paraffin embedded (FFPE) tumor tissue specimens); VENTANA ALK (D5F3) CDx Assay (qualitative detection of the anaplastic lymphoma kinase (ALK) protein in formalin-fixed, paraffin-embedded (FFPE) non-small cell lung carcinoma (NSCLC) tissue stained with the BenchMark XT or BenchMark ULTRA automated staining instrument); and Vysis ALK Break Apart FISH Probe Kit test (a qualitative test to detect rearrangements involving the ALK gene via fluorescence in situ hybridization (FISH) in formalin-fixed, paraffin-embedded (FFPE) non-small cell lung cancer (NSCLC) tissue specimens). In one embodiment, the test is a fluorescence in situ hybridization (FISH) test, e.g., Vysis ALK Break Apart FISH Probe Kit test. Additional information for FDA-approved tests can be found at, e.g., https://www.fda.gov/MedicalDevices/ProductsandMedicalProcedures/InVitroDiagnostics/ucm303030.htm; and additional information for Vysis ALK Break Apart FISH Probe Kit can be found at, e.g., https://www.molecular.abbott/us/en/products/oncology/vysis-alk-break-apart-fish-probe-kit; the entirety of which are incorporated herein by reference.

In one embodiment, the cancer is a solid tumor. In one embodiment, the cancer is an advanced solid tumor. In one embodiment, the cancer is an ALK+ advanced solid tumor. In one embodiment, the cancer is an ALK+ advanced solid tumor that has failed one or more prior standard of care (SOC) treatment(s).

In one embodiment, the cancer is neuroblastoma. In one embodiment, the cancer is relapsed or refractory neuroblastoma. In one embodiment, the cancer is relapsed neuroblastoma. In one embodiment, the cancer is refractory neuroblastoma. In one embodiment, the cancer is ALK+ neuroblastoma. In one embodiment, the cancer is relapsed or refractory ALK+ neuroblastoma.

In one embodiment, the cancer is inflammatory myofibroblastic tumor (IMT). In one embodiment, the cancer is unresectable or recurrent IMT. In one embodiment, the cancer is unresectable IMT. In one embodiment, the cancer is recurrent IMT. In one embodiment, the cancer is ALK+ IMT. In one embodiment, the cancer is unresectable or recurrent ALK+IMT.

In one embodiment, the cancer is a hematological cancer. In one embodiment, the cancer is a lymphoma, leukemia, or myeloma. In one embodiment, the cancer is a lymphoma. In one embodiment, the cancer is a non-Hodgkin lymphoma. In one embodiment, the cancer is anaplastic large cell lymphoma (ALCL). In one embodiment, the cancer is relapsed or refractory ALCL. In one embodiment, the cancer is relapsed ALCL. In one embodiment, the cancer is refractory ALCL. In one embodiment, the cancer is ALK+ ALCL. In one embodiment, the cancer is relapsed or refractory ALK+ ALCL. In one embodiment, the cancer is newly diagnosed ALCL. In one embodiment, the cancer is newly diagnosed ALCL with high risk for recurrence. In one embodiment, the cancer is newly diagnosed ALK+ ALCL with high risk for recurrence.

Several traits associated with high risk of recurrence have been identified among ALCL patients. The presence of one or more of the characteristics of mediastinal involvement, visceral involvement defined as lung, liver, or spleen involvement, and skin involvement are all prognostic for recurrence by multivariate analysis. Le Deley et al., *Blood* 2008, 111(3), 1560-6; Le Deley et al., *Journal of Clinical Oncology* 2010, 28(25), 3987-93. Other factors that may be associated with high risk for treatment failure in children with ALCL include NPM1-ALK in peripheral blood by polymerase chain reaction (PCR) and/or infiltration in the bone marrow that is detectable through molecular techniques at diagnosis (i.e., minimal disseminated disease (MDD)), low anti-ALK antibody titers at diagnosis, and detection of minimal residual disease (MRD) by PCR for NPM1-ALK in the blood after the first course of chemotherapy. Damm-Welk et al., 2007; Mussolin et al., *Leukemia* 2005, 19(9), 1643-7; Ait-Tahar et al., *Blood* 2010, 115(16), 3314-9; Damm-Welk et al., *Blood* 2014, 123(3), 334-7; Turner et al., 2016.

Mussolin and colleagues investigated the prognostic value of MDD and anti-ALK immune response in children with NPM-ALK+ ALCL to determine whether risk of recurrence could be stratified by these factors. Mussolin et al., 2013. Among 128 patients included in the study, 26 (20%) were considered to have high-risk disease based on the presence of MDD+ status and an antibody titer ≤1/750. Five-year PFS and overall survival (OS) were 28% and 72% among this high-risk group of patients. In contrast, PFS/OS were 93%/98% for low-risk patients (MDD− with an antibody titer >1/750) and 68%/84% among intermediate-risk patients (MDD− and antibody titer ≤1/750 or MDD+ and antibody titer >1/750).

In one embodiment, the high risk for recurrence is characterized by the presence of one or more characteristics selected from mediastinal involvement, visceral involvement defined as lung, liver, or spleen involvement, skin involvement, NPM1-ALK in peripheral blood, infiltration in the bone marrow, low anti-ALK antibody titers at diagnosis, and detection of minimal residual disease (MRD) for NPM1-ALK in the blood after the first course of chemotherapy. In one embodiment, the high risk for recurrence is characterized minimal disseminated disease positive (MDD+) at diagnosis. In one embodiment, the high risk for recurrence is characterized by low anti-ALK antibody titer at diagnosis. In one embodiment, the high risk for recurrence is characterized by anti-ALK antibody titer ≤1/750 at diagnosis.

In one embodiment, Compound A, or a pharmaceutically acceptable salt thereof, is administered orally. In one embodiment, Compound A, or a pharmaceutically acceptable salt thereof, is administered as a tablet. In one embodiment, the tablet is in 30 mg, 90 mg, or 180 mg dose strength of Compound A. In one embodiment, the tablet is a white film-coated tablet.

Compound A, or a pharmaceutical acceptable salt thereof, can be administered once daily (QD), or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of Compound A, or a pharmaceutical acceptable salt thereof, is administration for one to six days per week, administration in cycles (e.g., daily administration for two to eight consecutive weeks, then a rest period with no administration for up to one week), or administration on alternate days.

In one embodiment, Compound A, or a pharmaceutically acceptable salt thereof, is administered once a day (QD). In one embodiment, Compound A, or a pharmaceutically acceptable salt thereof, is administered twice a day (BID).

In certain embodiments, Compound A, or a pharmaceutical acceptable salt thereof, is cyclically administered to a patient. Cycling therapy involves the administration of an active agent for a period of time, followed by a rest for a period of time, and repeating this sequential administration. Cycling therapy can avoid or reduce the side effects of one of the therapies, and/or improves the efficacy of the treatment.

In one embodiment, Compound A, or a pharmaceutically acceptable salt thereof, is administered at a dose of from about 10 mg/m$^2$ to about 150 mg/m$^2$. In one embodiment, Compound A, or a pharmaceutically acceptable salt thereof, is administered at a dose of from about 30 mg/m$^2$ to about 100 mg/m$^2$. In one embodiment, Compound A, or a pharmaceutically acceptable salt thereof, is administered at a dose of from about 30 mg/m$^2$ to about 60 mg/m$^2$. In one embodiment, Compound A, or a pharmaceutically acceptable salt thereof, is administered at a dose of from about 40 mg/m$^2$ to about 80 mg/m$^2$. In one embodiment, Compound A, or a pharmaceutically acceptable salt thereof, is administered at a dose of from about 40 mg/m$^2$ to about 100 mg/m$^2$.

In one embodiment, Compound A, or a pharmaceutically acceptable salt thereof, is administered at a dose of about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, or about 150 mg/m$^2$. In one embodiment, Compound A, or a pharmaceutically acceptable salt thereof, is administered at a dose of about 30, about 40, about 50, about 60, about 70, about 80, about 90, or about 100 mg/m$^2$. In one embodiment, Compound A, or a pharmaceutically acceptable salt thereof, is administered at a dose of about 10 mg/m$^2$. In one embodiment, Compound A, or a pharmaceutically acceptable salt thereof, is administered at a dose of about 20 mg/m$^2$. In one embodiment, Compound A, or a pharmaceutically acceptable salt thereof, is administered at a dose of about 30 mg/m$^2$. In one embodiment, Compound A, or a pharmaceutically acceptable salt thereof, is administered at a dose of about 40 mg/m$^2$. In one embodiment, Compound A, or a pharmaceutically acceptable salt thereof, is administered at a dose of about 50 mg/m$^2$. In one embodiment, Compound A, or a pharmaceutically acceptable salt thereof, is administered at a dose of about 60 mg/m$^2$. In one embodiment, Compound A, or a pharmaceutically acceptable salt thereof, is administered at a dose of about 70 mg/m$^2$. In one embodiment, Compound A, or a pharmaceutically acceptable salt thereof, is administered at a dose of about 80 mg/m$^2$. In one embodiment, Compound A, or a pharmaceutically acceptable salt thereof, is administered at a dose of about 90 mg/m$^2$. In one embodiment, Compound A, or a pharmaceutically acceptable salt thereof, is administered at a dose of about 100 mg/m$^2$. In one embodiment, Compound A, or a pharmaceutically acceptable salt thereof, is administered at a dose of about 110 mg/m$^2$. In one embodiment, Compound A, or a pharmaceutically acceptable salt thereof, is administered at a dose of about 120 mg/m$^2$. In one embodiment, Compound A, or a pharmaceutically acceptable salt thereof, is administered at a dose of about 130 mg/m$^2$. In one embodiment, Compound A, or a pharmaceutically acceptable salt thereof, is administered at a dose of about 140 mg/m$^2$. In one embodiment, Compound A, or a pharmaceutically acceptable salt thereof, is administered at a dose of about 150 mg/m$^2$.

In one embodiments, Compound A, or a pharmaceutical acceptable salt thereof, is administered in a sufficient amount to achieve an area under the curve (AUC) exposure in pediatric patients that would not exceed 80% of those achieved at the clinical dose in adults.

In one embodiments, Compound A, or a pharmaceutical acceptable salt thereof, is administered in a sufficient amount to provide $AUC_\infty$ of Compound A in the range from about 1000 to about 40000 ng·hr/mL, from about 2000 to about 30000 ng·hr/mL, from about 4000 to about 25000 ng·hr/mL, or from about 5000 to about 20000 ng·hr/mL. In one embodiments, Compound A, or a pharmaceutical acceptable salt thereof, is administered in a sufficient amount to provide $AUC_\infty$ of Compound A in the range from about 4000 to about 25000 ng·hr/mL. In one embodiments, Compound A, or a pharmaceutical acceptable salt thereof, is administered in a sufficient amount to provide $AUC_\infty$ of Compound A in the range from about 5000 to about 20000 ng·hr/mL. In one embodiments, Compound A, or a pharmaceutical acceptable salt thereof, is administered in a sufficient amount to provide $AUC_\infty$ of Compound A of about 10000 ng·hr/mL.

In one embodiment, Compound A (i.e., free base) is administered. In one embodiment, a pharmaceutically acceptable salt (e.g., HCl salt) of Compound A is administered. In one embodiment, the administered amount refers to the amount as measured in the amount of Compound A.

In one embodiment, Compound A, or a pharmaceutically acceptable salt thereof, can be administered as a monotherapy or in a combination therapy with one or more second therapeutic agents. In one embodiment, the methods provided herein further comprises administering to the patient a therapeutically effective amount of a second therapeutic agent.

In one embodiment, provided herein is a method for treating a cancer in a pediatric patient having the cancer, comprising administering to the patient a therapeutically effective amount of Compound A, or a pharmaceutically acceptable salt thereof, in combination with a second therapeutic agent.

In one embodiment, the second therapeutic agent is the ALCL99 chemotherapy regimen. This regimen is derived from the BFM protocol previously used in aggressive B-cell NHL. Treatment regimens differ somewhat across studies but typically involve cyclophosphamide, doxorubicin, vincristine, corticosteroids, ifosfamide, and etoposide given for 4 to 6 months, with high-dose methotrexate and cytarabine for central nervous system (CNS) prophylaxis. Eyre et al., 2014; Turner et al., 2016.

In one embodiment, the second therapeutic agent is cyclophosphamide, doxorubicin, vincristine, corticosteroid, ifosfamide, etoposide, methotrexate, or cytarabine, or a combination thereof. In one embodiment, the corticosteroid is dexamethasone or hydrocortisone, or a combination thereof.

In one embodiment, the second therapeutic agent includes dexamethasone. In one embodiment, the second therapeutic agent includes dexamethasone, which is administered at a dose of from about 2.5 mg/m² to about 20 mg/m². In one embodiment, the second therapeutic agent includes dexamethasone, which is administered at a dose of from about 5 mg/m² to about 10 mg/m². In one embodiment, the second therapeutic agent includes dexamethasone, which is administered at a dose of about 5 mg/m². In one embodiment, the second therapeutic agent includes dexamethasone, which is administered at a dose of about 10 mg/m².

In one embodiment, the second therapeutic agent includes cyclophosphamide. In one embodiment, the second therapeutic agent includes cyclophosphamide, which is administered at a dose of from about 100 mg/m² to about 300 mg/m². In one embodiment, the second therapeutic agent includes cyclophosphamide, which is administered at a dose of about 200 mg/m².

In one embodiment, the second therapeutic agent includes ifosfamide. In one embodiment, the second therapeutic agent includes ifosfamide, which is administered at a dose of from about 400 mg/m² to about 1200 mg/m². In one embodiment, the second therapeutic agent includes ifosfamide, which is administered at a dose of about 800 mg/m².

In one embodiment, the second therapeutic agent includes methotrexate. In one embodiment, the second therapeutic agent includes methotrexate, which is administered at a dose of from about 1.5 g/m² to about 4.5 g/m². In one embodiment, the second therapeutic agent includes methotrexate, which is administered at a dose of about 3 g/m².

In one embodiment, the second therapeutic agent includes etoposide. In one embodiment, the second therapeutic agent includes etoposide, which is administered at a dose of from 50 mg/m² to about 150 mg/m². In one embodiment, the second therapeutic agent includes etoposide, which is administered at a dose of about 100 mg/m².

In one embodiment, the second therapeutic agent includes cytarabine. In one embodiment, the second therapeutic agent includes cytarabine, which is administered at a dose of from about 75 mg/m² to about 225 mg/m² and is administered twice a day. In one embodiment, the second therapeutic agent includes cytarabine, which is administered at a dose of about 150 mg/m² and is administered twice a day.

In one embodiment, the second therapeutic agent includes doxorubicin. In one embodiment, the second therapeutic agent includes doxorubicin, which is administered at a dose of from 12.5 mg/m² to about 37.5 mg/m². In one embodiment, the second therapeutic agent includes doxorubicin, which is administered at a dose of about 25 mg/m².

In certain embodiments, Compound A, or a pharmaceutically acceptable salt thereof, and the second therapeutic agent are cyclically administered to a patient. Cycling therapy involves the administration of an active agent for a period of time, followed by a rest for a period of time, and repeating this sequential administration. Cycling therapy can avoid or reduce the side effects of one of the therapies, and/or improves the efficacy of the treatment.

In one embodiment, Compound A, or a pharmaceutically acceptable salt thereof, and the second therapeutic agent are administered for one or more 7 days cycles. In one embodiment, Compound A, or a pharmaceutically acceptable salt thereof, and the second therapeutic agent are administered for one or more 21 days cycles. In one embodiment, Compound A, or a pharmaceutically acceptable salt thereof, and the second therapeutic agent are administered for one or more 28 days cycles.

In one embodiment, Compound A, or a pharmaceutically acceptable salt thereof, and the second therapeutic agent are administered for at least 4 cycles. In one embodiment, Compound A, or a pharmaceutically acceptable salt thereof, and the second therapeutic agent are administered for at least 6 cycles. In one embodiment, Compound A, or a pharmaceutically acceptable salt thereof, and the second therapeutic agent are administered for at least 8 cycles. In one embodiment, Compound A, or a pharmaceutically acceptable salt thereof, and the second therapeutic agent are administered for at least 12 cycles.

In one embodiment, Compound A, or a pharmaceutically acceptable salt thereof, is administered on days 1-21 of the 21 days cycle.

In one embodiment, the second therapeutic agent includes dexamethasone, which is administered on days 1-5 of the 21 days cycle.

In one embodiment, the second therapeutic agent includes cyclophosphamide, which is administered on days 1 and 2 of the 21 day cycle.

In one embodiment, the second therapeutic agent includes cyclophosphamide, which is administered on days 1-5 of the 21 day cycle.

In one embodiment, the second therapeutic agent includes a combination of hydrocortisone, methotrexate, and cytarabine, which are administered on day 1 of the 21 days cycle.

In one embodiment, the second therapeutic agent includes ifosfamide, which is administered on days 1-5 of the 21 days cycle.

In one embodiment, the second therapeutic agent includes methotrexate, which is administered on day 1 of the 21 days cycle.

In one embodiment, the second therapeutic agent includes etoposide, which is administered on days 4 and 5 of the 21 days cycle.

In one embodiment, the second therapeutic agent includes cytarabine, which is administered on days 4 and 5 of the 21 days cycle.

In one embodiment, the second therapeutic agent includes doxorubicin, which is administered on days 4 and 5 of the 21 days cycle.

In one embodiment, provided herein is a method for treating unresectable or recurrent IMT in a pediatric patient, comprising administering to the patient a therapeutically effective amount of Compound A, or a pharmaceutically acceptable salt thereof. In one embodiment, the IMT is unresectable or recurrent ALK+IMT. In one embodiment, Compound A, or a pharmaceutically acceptable salt thereof, is administered at a dose of from about 30 mg/m$^2$ to about 100 mg/m$^2$. In one embodiment, Compound A, or a pharmaceutically acceptable salt thereof, is administered at a dose of about 30 mg/m$^2$. In one embodiment, Compound A, or a pharmaceutically acceptable salt thereof, is administered at a dose of about 40 mg/m$^2$. In one embodiment, Compound A, or a pharmaceutically acceptable salt thereof, is administered at a dose of about 60 mg/m$^2$. In one embodiment, Compound A, or a pharmaceutically acceptable salt thereof, is administered at a dose of about 80 mg/m$^2$. In one embodiment, Compound A, or a pharmaceutically acceptable salt thereof, is administered at a dose of about 100 mg/m$^2$.

In one embodiment, provided herein is a method for treating relapsed or refractory ALCL in a pediatric patient, comprising administering to the patient a therapeutically effective amount of Compound A, or a pharmaceutically acceptable salt thereof. In one embodiment, the ALCL is relapsed or refractory ALK+ ALCL. In one embodiment, Compound A, or a pharmaceutically acceptable salt thereof, is administered at a dose of from about 30 mg/m$^2$ to about 100 mg/m$^2$. In one embodiment, Compound A, or a pharmaceutically acceptable salt thereof, is administered at a dose of about 30 mg/m$^2$. In one embodiment, Compound A, or a pharmaceutically acceptable salt thereof, is administered at a dose of about 40 mg/m$^2$. In one embodiment, Compound A, or a pharmaceutically acceptable salt thereof, is administered at a dose of about 60 mg/m$^2$. In one embodiment, Compound A, or a pharmaceutically acceptable salt thereof, is administered at a dose of about 80 mg/m$^2$. In one embodiment, Compound A, or a pharmaceutically acceptable salt thereof, is administered at a dose of about 100 mg/m$^2$.

In one embodiment, provided herein is a method for treating ALCL in a pediatric patient, comprising administering to the patient a therapeutically effective amount of Compound A, or a pharmaceutically acceptable salt thereof, in combination of an ALCL99 regimen.

In one embodiment, provided herein is a method for treating ALCL in a pediatric patient, comprising administering to the patient a therapeutically effective amount of Compound A, or a pharmaceutically acceptable salt thereof, in combination of dexamethasone, ifosfamide, methotrexate, etoposide, and cytarabine. In one embodiment, the treatment continues for one or more 21 days cycles. In one embodiment, Compound A, or a pharmaceutically acceptable salt thereof, is administered on days 1-21 of the 21 days cycle; dexamethasone is administered on days 1-5 of the 21 days cycle; ifosfamide is administered on days 1-5 of the 21 days cycle; methotrexate is administered on day 1 of the 21 days cycle; etoposide is administered on days 4 and 5 of the 21 days cycle; and cytarabine is administered on days 4 and 5 of the 21 days cycle. In one embodiment, Compound A, or a pharmaceutically acceptable salt thereof, is administered on days 1-21 of the 21 days cycle; dexamethasone is administered at a dose of about 10 mg/m$^2$ on days 1-5 of the 21 days cycle; ifosfamide is administered at a dose of about 800 mg/m$^2$ on days 1-5 of the 21 days cycle; methotrexate is administered at a dose of about 3 g/m$^2$ (e.g., over 3 hours) on day 1 of the 21 days cycle; etoposide is administered at a dose of about 100 mg/m$^2$ on days 4 and 5 of the 21 days cycle; and cytarabine is administered at a dose of about 150 mg/m$^2$ twice a day on days 4 and 5 of the 21 days cycle.

In one embodiment, provided herein is a method for treating ALCL in a pediatric patient, comprising administering to the patient a therapeutically effective amount of Compound A, or a pharmaceutically acceptable salt thereof, in combination of dexamethasone, methotrexate, cyclophosphamide, and doxorubicin. In one embodiment, the treatment continues for one or more 21 days cycles. In one embodiment, Compound A, or a pharmaceutically acceptable salt thereof, is administered on days 1-21 of the 21 days cycle; dexamethasone is administered on days 1-5 of the 21 days cycle; methotrexate is administered on day 1 of the 21 days cycle; cyclophosphamide is administered on days 1-5 of the 21 days cycle; and doxorubicin is administered on days 4 and 5 of the 21 days cycle. In one embodiment, Compound A, or a pharmaceutically acceptable salt thereof, is administered on days 1-21 of the 21 days cycle; dexamethasone is administered at a dose of about 10 mg/m$^2$ on days 1-5 of the 21 days cycle; methotrexate is administered at a dose of about 3 g/m$^2$ (e.g., over 3 hours) on day 1 of the 21 days cycle; cyclophosphamide is administered at a dose of about 200 mg/m$^2$ on days 1-5 of the 21 days cycle; and doxorubicin is administered at a dose of about 25 mg/m$^2$ on days 4 and 5 of the 21 days cycle.

Pharmaceutical Compositions

Also provided herein are pharmaceutical compositions that are useful for the methods provided herein. The therapeutic agents used in the methods provided herein, individually or any combination thereof, can be comprised in same or different pharmaceutical compositions.

In one embodiment, provided herein are pharmaceutical compositions and dosage forms, which comprise Compound A, or a pharmaceutically acceptable salt thereof. In one embodiment, pharmaceutical compositions and dosage forms further comprise one or more excipients.

In one embodiment, provided herein are pharmaceutical compositions and dosage forms, which comprise Compound A, or a pharmaceutically acceptable salt thereof, and lactose monohydrate, microcrystalline cellulose, sodium starch glycolate (Type A), magnesium stearate, and hydrophobic colloidal silica.

In one embodiment, brigatinib (Compound A) is supplied for oral use as film-coated tablets containing 30 mg, 90 mg, or 180 mg of brigatinib and the following inactive ingredients: lactose monohydrate, microcrystalline cellulose, sodium starch glycolate (Type A), magnesium stearate, and hydrophobic colloidal silica. The tablet coating consists of talc, polyethylene glycol, polyvinyl alcohol, and titanium dioxide.

Additional pharmaceutical formulations comprising brigatinib are described in international application No. PCT/US2018/021128, which is incorporated herein by reference.

Further Combination Therapies

Also provided herein are methods for further combination therapies in which, in addition to a first therapeutic agent provided herein (e.g., Compound A) and a second therapeutic agent provided herein (e.g., ALCL99 chemotherapy regimen), one or more agents (e.g., a third therapeutic agent or therapy) known to modulate other pathways, or the same pathway, may be used. In certain embodiments, such methods comprise administering to a subject in need thereof. Compound A, optionally in combination with an ALCL99 chemotherapy regimen, and further in combination with one or more additional therapeutic agents such as anticancer agents, chemotherapeutic agents, therapeutic antibodies, and radiation treatment, to provide, where desired, a synergistic or additive therapeutic effect.

The route of administration of the third therapeutic agent or therapy is independent of the route of administration of the first and second agents. The third therapeutic agent or therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

One or more third active ingredients or agents can be used in the methods provided herein. Third active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins.

Third active agents that are small molecules can also be used to alleviate adverse effects associated with the administration of a combination therapy provided herein. However, like some large molecules, many are believed to be capable of providing an additive or synergistic effect when administered with (e.g., before, after or simultaneously) a combination provided herein. Examples of small molecule third active agents include, but are not limited to, anti-cancer agents, antibiotics, immunosuppressive agents, and steroids.

Examples of additional anti-cancer agents to be used within the methods or compositions described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; clofarabine; crisnatol mesylate; cyclophosphamide; cytarabine; dacarbazine; dabrafenib; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; paclitaxel protein-bound particles for injectable suspension (albumin-bound); pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; vemurafenib; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods or compositions include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogens; antiestrogens; antineoplastons; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitors; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogs; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; Ara-C ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogs; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitors; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogs; lipophilic disaccharide peptides; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitors; mifepristone; miltefosine; mirimostim; mitoguazone; mitolactol; mitomycin analogs; mitonafide; mitotoxin fibroblast growth factor-saporin; mitoxantrone; mofarotene; molgramostim; cetuximab, human chorionic gonadotrophin; monophosphoryl lipid A+*mycobacterium* cell wall skeleton; mopidamol; mustard anticancer agents; mycaperoxide B; mycobacterial cell wall extract; myriaporone; N-acetyldinaline; N-sub stituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidants; nitrullyn; oblimersen (Genasense®); O$^6$-benzylguanine; octreotide; okicenone; oligonucleotides; onapristone; ondansetron; ondansetron; oracin; oral cytokine inducers; ormaplatin; osaterone; oxaliplatin; oxaunomycin; paclitaxel; paclitaxel analogs; paclitaxel derivatives; paclitaxel protein-bound particles for injectable suspension (albumin-bound); palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitors; platinum complexes; platinum compounds; platinum-triamine complexes; porfimer sodium; porfiromycin; prednisone; propyl bis-acridone; prostaglandin J2; proteasome inhibitors; protein A-based immune modulators; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugates; raf antagonists; raltitrexed; ramosetron; ras farnesyl protein transferase inhibitors; ras inhibitors; ras-GAP inhibitors; retelliptine demethylated; rhenium Re 186 etidronate; rhizoxin; ribozymes; RII retinamide; rohitukine; romurtide; roquinimex; rubiginone B 1; ruboxyl; safingol; saintopin; sarmustine; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonists; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonists; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Other third active agents useful in the methods or compositions include, but are not limited to, rituximab, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, gefitinib (Iressa®), taxol, taxotere, fluorouracil, leucovorin, irinotecan, xeloda, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, interleukin 2, ganulocyte-macrophage colony-stimulating factor, dacarbazine, vinorelbine, zoledronic acid, palmitronate, biaxin, busulphan, prednisone, bisphosphonate, arsenic trioxide, vincristine, doxorubicin (Doxil®), paclitaxel, paclitaxel protein-bound particles for injectable suspension (albumin-bound), ganciclovir, adriamycin, estramustine sodium phosphate (Emcyt®), sulindac, and etoposide.

Other specific third active agents useful in the methods or compositions include, but are not limited to, sorafenib, dabrafenib, vemurafenib, trametinib, cobimetinib, binimetinib, selumetinib, PD-325901, CI-1040 (PD184352), TAK-733, AT7867, AZD 8055, BX-912, silmitasertib, pictilisib, MK-2206, pilaralisib, gefitinib, erlotinib, lapatinib, osimertinib, OSI-027, AZD8055, sapanisertib, Dactolisib, BGT226, voxtalisib, apitolisib, omipalisib, PF-04691502, gedatolisib, PP242, lenalidomide, or pomalidomide.

Medical Kits

Also provided herein are medical kits. In certain embodiments, provided herein is a medical kit comprising Compound A, or a pharmaceutically acceptable salt thereof.

In certain embodiments, the kits comprise Compound A or a pharmaceutically acceptable salt thereof, and a second therapeutic agent as described herein, in suitable packaging, and written materials that can comprise instructions for use, discussion of clinical studies, listing of side effects, and the like. In certain embodiments, such kits may also comprise information, such as, for example, scientific literature references, package insert materials, clinical trial results, and/or summaries of these and the like, which indicate or establish the activities and/or advantages of the composition, and/or which describe dosing, administration, side effects, drug interactions, or other information useful to the health care provider. In certain embodiments, such information may be based on the results of various studies, for example, studies using experimental animals involving in vivo models and studies based on human clinical trials. In certain embodiments, the kit may further comprise another agent. In certain embodiments, Compound A or a pharmaceutically acceptable salt thereof of the present disclosure and a second therapeutic agent are provided as separate compositions in separate containers within the kit. In certain embodiments, Compound A or a pharmaceutically acceptable salt thereof of the present disclosure and a second therapeutic agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

EXAMPLES

Example 1: Extrapolation and Interrelation Between Adult and Pediatric Populations As no pediatric clinical PK data are currently available for brigatinib, the projection of pediatric clinical PK of brigatinib from adult PK was performed using an allometric approach. The key aspects of this analysis are summarized below.

The use of an allometric scaling approach is supported by knowledge of clearance mechanisms for brigatinib and their corresponding ontogeny, which indicate maturation of clearance in pediatric patients of >1 year of age. Accordingly, simulations based on a previously developed population PK model have been performed to guide dose selection for the pediatric phase 1 dose-confirmation study taking into consideration the dosing regimen in adults for ALK+ NSCLC. The proposed study is an open-label phase 1 dose escalation in patients ≥2 years and with measurable or evaluable ALK+ solid or CNS tumors, or ALCL, refractory to therapy and for whom there is no known curative treatment available.

In the pivotal phase 2 study in adults with ALK+ NSCLC, 2 dose regimens were evaluated: (1) 90 mg QD; (2) 90 mg QD in Week 1 followed by escalation to 180 mg QD for those patients tolerating the 7-day 90 mg QD lead in. Based on demonstration of longer PFS at 180 mg QD, the recommended clinical dose of brigatinib in adults is 90 mg orally QD for the first 7 days followed by a dose increase to 180 mg QD based upon patient tolerability. This approach of a 7-day lead in at a lower dose offers risk mitigation for EOPEs. Therefore, a similar dosing regimen is proposed in pediatric development with a 7-day lead-in period. To mitigate the risk for EOPEs in pediatric patients, the doses of brigatinib selected for Week 1 of treatment are informed by adult clinical experience and designed to achieve systemic exposures not exceeding those at the 90 mg daily dose in adults.

The adult population PK model described brigatinib PK using a 3-compartment model with a transit absorption compartment model. The final covariate model included linear functions relating body weight to clearance and volume parameters. In addition, age and albumin concentration were deemed to be statistically significant covariates on clearance.

For the purposes of simulating pediatric PK, the linear covariate functions relating body weight to clearance and volume parameters were replaced with allometric functions, which employed scaling coefficients (i.e., exponents) of 0.75 for clearance and 1 for volume parameters. The adapted model was used to derive, through simulation, the posology in pediatric patients that would achieve exposures similar to those observed in adult patients after a reference dose of 90 mg QD. Virtual pediatric patients were simulated based on body size vs age distributions in the National Health and Nutrition Examination Survey (NHANES) dataset provided by the Centers for Disease Control and Prevention (CDC). The pediatric patient population was stratified by age (1000 patients in each month of age; 1 to 18 years) and sex (50:50; male:female).

Based on a cross-study comparison of brigatinib exposure from an oral solution administered in the human radioactive mass balance study (Study AP26113-13-104) and from tablet PK in adults (Study AP26113-16-110), the relative bioavailability of an oral brigatinib solution is anticipated to be approximately 42% higher in terms of AUC in reference to the tablet. Therefore, a relative bioavailability factor (oral solution/tablet AUC ratio of 1.42) was incorporated in the pediatric simulations.

Simulations using the adapted model indicated that brigatinib exposures in pediatric patients aged 1 to less than 18 years of age following administration of 40 mg/m$^2$ brigatinib as an oral solution would be comparable to those achieved in adult patients receiving 90 mg QD as an oral tablet (FIG. 1).

Based on these simulations, systemic exposures in pediatric patients receiving doses of 40 mg/m$^2$ QD→80 mg/m$^2$ QD are expected to be comparable to those achieved at the adult recommended clinical dose of 90 mg QD→180 mg QD. In the planned pediatric phase 1 study, the starting dose level (30 mg/m$^2$ QD→60 mg/m$^2$ QD; Dose Level 1) was selected to achieve model-predicted pediatric exposures (AUC) that would not exceed 80% of those achieved at the clinical dose in adults (90 mg QD→180 mg QD), consistent with typically utilized approaches in pediatric phase 1 studies. The planned subsequent dose level (40 mg/m$^2$ QD→80 mg/m$^2$ QD; Dose Level 2) is expected to achieve 100% of adult exposures. One additional dose level is planned if the 40 mg/m$^2$ QD→80 mg/m$^2$ QD dose is tolerated. To mitigate the risk for EOPEs, the Week 1 brigatinib dose in Dose Level 3 (40 mg/m$^2$ QD→100 mg/m$^2$ QD) is 40 mg/m$^2$ QD (i.e., a dose level expected to provide systemic exposures that match those achieved in adults at the 90 mg QD lead-in dose). The 100 mg/m$^2$ QD maximum planned dose was selected to achieve systemic exposures approximately comparable to those at the highest acceptably tolerated dose of 240 mg QD in adults in Study AP26113-11-101.

The rationale for continued escalation in the pediatric population beyond Dose Level 2 was informed by the following considerations:

Adult experience with brigatinib in ALK+ NSCLC where longer PFS was observed at 90 mg QD→180 mg QD vs. 90 mg QD doses, suggesting that it cannot be assumed that exposures associated with 180 mg QD would maximize efficacy in ALK+ pediatric cancers.

Pediatric clinical experience with the ALK inhibitor crizotinib that achieved a MTD/RP2D of 280 mg/m$^2$ with an associated systemic exposure that is ~50% higher than adult clinical exposures at 250 mg BID.

For these reasons, a direct extrapolation approach is not proposed for the pediatric development of brigatinib. Instead, clinical experience in adults as well as available pediatric and adult data on the ALK inhibitor crizotinib have been leveraged, with dose selection for the pediatric phase 1 program informed by population PK modeling and simulation. Similarly, population PK modeling of the pediatric phase 1 PK data will be used to guide dose selection for subsequent efficacy and safety studies in pediatric patient populations Example 2: Pediatric Clinical Studies General Strategy Two clinical studies in patients aged 2 years and older with ALCL or IMT are conducted for brigatinib: (a) an open-label, phase ½ dose-escalation and expansion study (Study 1) and (b) a phase 2 randomized study (Study 2).

During the phase 1 portion of Study 1, dose escalation of brigatinib monotherapy occurs according to a Rolling-6 design in subjects with any advanced ALK+ solid tumor or ALK+ ALCL that failed prior standard of care treatment (Part A-1). After the RP2D of brigatinib monotherapy is determined, phase 2 disease-specific expansion cohorts open and enroll patients with unresectable or recurrent ALK+IMT (Part B, Cohort B-1) or relapsed/refractory ALK+ ALCL (Part B, Cohort B-2). At this time, dose escalation is also initiated with brigatinib in combination with a standard chemotherapy regimen (ALCL99 regimen) among newly diagnosed ALK+ ALCL patients at high risk for recurrence to determine the RP2D of brigatinib when used in combination with ALCL99 (Part A-2).

The sample size for Cohort B-1 of Study 1 is approximately 28 subjects.

Study 2 is initiated if sufficient safety, tolerability, and preliminary efficacy are observed among ALCL patients in Parts A-2 and B of Study 1. The patient population enrolled in Study 2 includes pediatric patients with previously untreated ALK+ ALCL at high risk for recurrence, defined as MDD+ status and low anti-ALK antibody titers (≤1/750) at diagnosis. This subgroup exhibits the highest unmet need and response to existing treatments, as evidenced by 5-year PFS and OS of 28% and 72%, respectively, and may benefit from more aggressive or diverse front-line interventions that drive deeper response, with the objective of preventing or forestalling relapse. In contrast, patients with low and intermediate risk exhibit much better response to current treatments with 5-year PFS/OS of 93%/98% and 68%/84, respectively. Mussolin et al., 2013. The study incorporates a randomized, comparator-controlled design to allow for rigorous evaluation of the safety and efficacy of the combination of ALCL99 with brigatinib versus ALCL99 alone.

The sample size for phase 2 study in previously untreated, high-risk ALCL is approximately 104 patients, who are randomized in a 1:1 fashion to receive brigatinib in combination with ALCL99 or ALCL99 alone.

Figure 2:
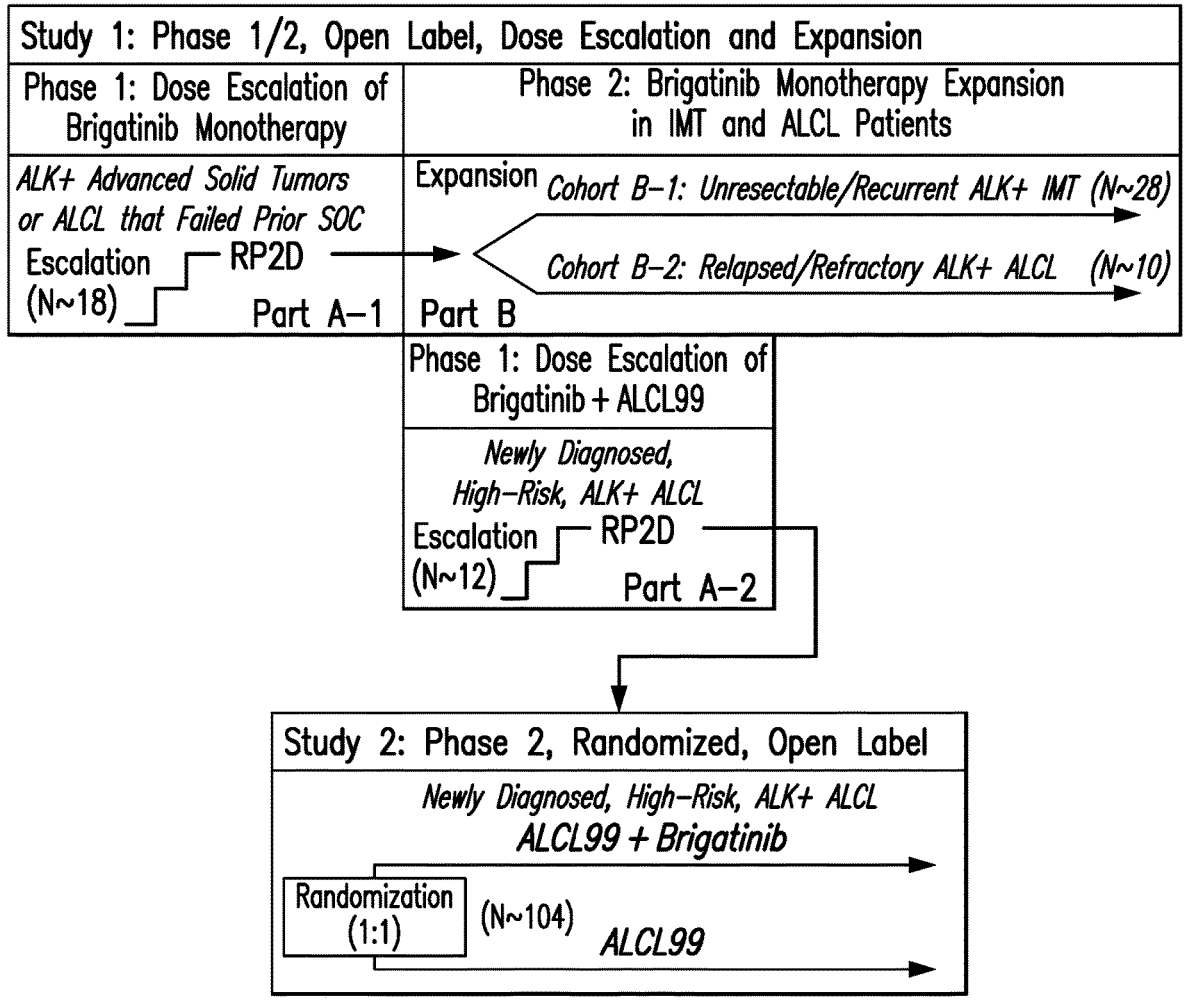
FIG. 2 shows the overview of clinical studies for brigatinib.

The designs of both clinical studies are illustrated in FIG. 2.

Pediatric PK/PD Studies

Serial plasma samples are collected during the phase 1 portion of the initial trial (Study 1) to characterize the PK of brigatinib in the pediatric population. Due to potential blood volume limitations, a sparser sampling scheme is used in younger children. An integrated population PK modeling approach is used, whereby the data from the phase 1 trial are combined with previously acquired PK data in healthy adult subjects and patients with NSCLC. Allometric functions are incorporated to estimate the effects of body size measures (e.g., body surface area [BSA], weight) on clearance and volume parameters. Sources of variability in the PK of brigatinib (i.e., covariates) are explored and previously estimated covariate effects in adults are updated based on the combined pediatric and adult dataset. Model performance is assessed by graphical evaluation of goodness-of-fit, statistical criteria, and visual predictive check. The model is used to derive exposure parameters for each pediatric subject and compared to the adult exposure metrics to guide further dose selection.

Patients in the pediatric phase 1 study are administered brigatinib as an oral solution. In subsequent studies, oral tablet formulation may be used in patients able to swallow solid oral dosage forms. The dosing approach for the tablet formulation (e.g., binned dosing) is informed by the integrated population PK analyses that are conducted using available adult data and pediatric data collected during the phase 1 study. The population PK analysis provides an updated estimate of the relative bioavailability of the oral solution formulation versus the tablet formulation.

PK data are obtained in the phase 2 expansion cohorts of IMT and ALCL patients in the initial study (Study 1) and in the separate phase 2 study of ALCL patients (Study 2). Sparse PK data are collected with sampling schemes informed by the results of modeling of phase 1 pediatric PK data. Integrated population PK analyses of data collected across the pediatric clinical development program are performed to confirm adequacy of the proposed posology over the evaluated pediatric age range. The model is used to derive exposure parameters for each pediatric patient and contributes to assessment of exposure-efficacy and exposure-safety relationships for brigatinib in a pediatric population.

Clinical Efficacy and Safety Studies

Study 1: Phase 1/2 Study of Brigatinib in Patients Aged 2 Years and Older with Malignancies with a Genetic Alteration in Anaplastic Lymphoma Kinase (ALK)

Primary Objectives

To estimate the MTD/RP2D regimen of brigatinib monotherapy administered PO QD as a liquid formulation in a pediatric patient population.

To estimate the MTD/RP2D regimen of brigatinib administered PO QD as a liquid formulation in combination with the ALCL99 treatment regimen in pediatric patients with newly diagnosed high-risk ALK+ ALCL.

To assess the safety and tolerability of brigatinib administered as monotherapy and in combination with ALCL99 in a pediatric patient population.

To characterize the PK of brigatinib in a pediatric patient population administered as monotherapy and in combination with the ALCL99 treatment regimen.

Secondary Objectives

To define the antitumor activity of brigatinib within the disease-specific expansion cohorts (IMT and relapsed/refractory ALCL)

Primary Endpoints

Part A-1: Determination of brigatinib RP2D in monotherapy.

Part A-2: Determination of brigatinib RP2D in combination with ALCL99.

Part B Cohort B-1: ORR.

Part B Cohort B-2: ORR.

Secondary Endpoints

Part A-1 and A-2: MTD, DLTs, safety and tolerability, and PK.

Part B Cohorts B-1 and B-2: DOR, PFS, OS, safety, and tolerability.

Main Inclusion Criteria

For all Patients (Part A and B):

Patients must have a histologically or cytologically confirmed advanced solid tumor or lymphoma.

Patients are required to have an activating ALK aberration in their tumor detected by certified assay (i.e., Clinical Laboratory Improvement Amendments (CLIA) in the US) prior to screening. The report from this test is required to be submitted for eligibility. ALK immunohistochemistry can be used as a surrogate for fluorescence in situ hybridization (FISH) or next generation sequencing (NGS) for patients with IMT or ALCL.

Patients must not be receiving other investigational medications within 30 days of study entry or while on study.

Patient must meet the organ function and system function requirements as stated in the protocol.

For Part A-1:

Due to the unknown potential for early onset pulmonary adverse reactions in pediatric patient populations and the need for the monitoring of patient reportable symptoms such as dyspnea, patients must be ≥4 years of age (the lower age limit will be reduced to 2 years in subsequent cohorts after safety and tolerability data are reviewed).

Patients must have at least ONE of the following: (1) recurrent/progressive disease at any time prior to study enrollment, (2) refractory disease, (3) persistent disease.

Are refractory or intolerant to all available standard therapies.

Patients must have fully recovered from the acute toxic effects of all prior chemotherapy, immunotherapy, or radiotherapy prior to entering this study.

Patients must not be receiving any other anticancer agents or radiotherapy at the time of study entry or while on study.

For Part A-2:

Patients must be ≥2 years of age and <22 years of age.

Patients must have high-risk, ALK+ ALCL.

Patients must not have received any prior systemic chemotherapy.

For Part B, Cohort B-1:

Patients must be ≥2 years of age.

Have unresectable or recurrent ALK+IMT.

For Part B, Cohort B-2:

Patients must be ≥2 years of age and <22 years of age.

Have relapsed or refractory ALK+ ALCL.

Main Exclusion Criteria

Patients with symptomatic CNS metastases that are neurologically unstable or require an increasing dose of corticosteroids.

Patients receiving strong or moderate CYP3A inhibitors or inducers within 14 days prior to the first dose of study drug.

Previously received an ALK inhibitor (Part A-2 and Part B only).

Sample Size

Part A-1: Up to 18 evaluable patients ≥4 years of age with advanced ALK+ solid tumors or ALCL that failed prior standard of care. A minimum of 15 patients aged ≤18 years of age.

Part A-2: Up to 12 evaluable patients ≥2 and <22 years of age with newly diagnosed, high-risk ALCL. A minimum of 9 patients aged ≤18 years of age.

Part B, Cohort B-1: 28 patients aged ≥2 years of age with unresectable/recurrent IMT. A minimum of 15 patients aged ≤18 years of age.

Part B, Cohort B-2: 10 patients ≥2 and <22 years of age with relapsed/refractory ALCL. A minimum of 8 subjects ≤18 years of age.

Duration of Follow-Up

Patients experiencing either a PR or stable disease will continue to receive brigatinib as a single agent for up to 1 year upon agreement between the Sponsor and investigator until disease progression or unacceptable toxicity.

Treatments

BSA-based dosing of brigatinib is utilized to normalize systemic exposures over the planned age range. The 1-week lead-in paradigm (90 mg QD for 7 days followed by 180 mg QD continuously) recommended for adult patients with ALK+ NSCLC is utilized. The starting dose level was selected to achieve pediatric exposures (AUC) that does not exceed 80% of those achieved at the clinical dose in adults. The 100 mg/m$^2$ QD maximum planned dose is selected to achieve systemic exposures approximately comparable to those at the highest tolerated dose of 240 mg QD in adults.

Figure 3:
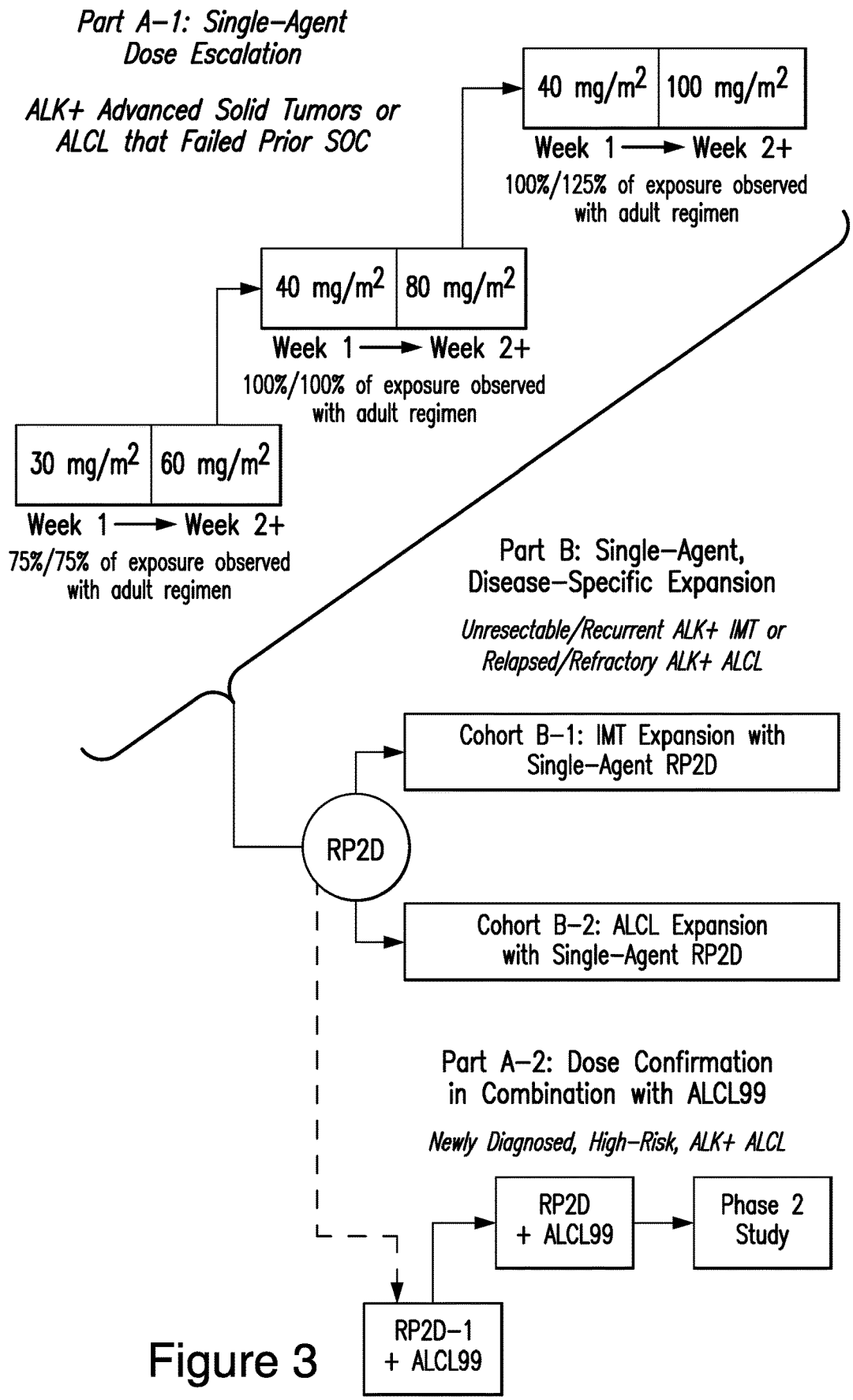
FIG. 3 shows the proposed doses for brigatinib for clinical study 1.

The doses proposed for each segment of the study are illustrated in FIG. 3.

The treatments to be administered in Study 1 are as follows:

Part A-1:

Brigatinib monotherapy (oral solution for all patients).

Part A-2:

Six cycles of ALCL99+/−brigatinib followed by brigatinib monotherapy.

| | |
|---|---|
| Prephase of ALCL99 | Dexamethasone: 5 mg/m$^2$ on Day 1-2, 10 mg/m$^2$ (divided into BID) on Days 3-5.<br>Cyclophosphamide: 200 mg/m$^2$ on Days 1 and 2.<br>Intrathecal Hydrocortisone, Methotrexate, Cytarabine (dose based on age): on Day 1.<br>Brigatinib will be administered on Days 1-21 of each course below as follows:<br>Brigatinib run-in dose on Days 1-7.<br>Brigatinib escalated dose on Day 8-onwards. |
| Course A (21-day cycle): | Brigatinib on Days 1-21.<br>Dexamethasone 10 mg/m$^2$ on Days 1-5.<br>Ifosfamide 800 mg/m$^2$ on Days 1-5.<br>Methotrexate 3 g/m$^2$ over 3 hours on Day 1.<br>Etoposide 100 mg/m$^2$ on Days 4 and 5.<br>Cytarabine 150 mg/m$^2$ x 2 on Days 4 and 5. |
| Course B (21-day cycle) | Brigatinib Day 1-21.<br>Dexamethasone 10 mg/m$^2$ on Days 1-5.<br>Methotrexate 3 g/m$^2$ over 3 hours on Day 1.<br>Cyclophosphamide 200 mg/m$^2$ on Days 1-5.<br>Doxorubicin 25 mg/m$^2$ on Days 4 and 5. |

Part B:

Brigatinib monotherapy. Oral solution and tablets (tablet doses for patients able to swallow solid oral dosage forms; tablet doses to be determined from PK data collected in Part A-1 and relative bioavailability considerations).

Duration of Treatment

For Part A-1 and Part B: Treatment continues until disease progression or unacceptable toxicity.

Part A-2: A total of 6 cycles of ALCL99+/−brigatinib are administered. Patients on either arm who experience a CR or CRu after 2 cycles of treatment may go on to transplant at the discretion of the investigator.

Patients experiencing either a PR or stable disease continue to receive brigatinib as single agent for up to 1 year upon agreement between the Sponsor and investigator until disease progression or unacceptable toxicity.

Statistical Considerations

Part A-1: Part A-1 of the study follows a Rolling-6 design. Two to 6 patients are accrued concurrently onto a dose level. Decisions as to which dose level to enroll a patient are based on the number of patients experiencing DLTs, and the number of patients still at risk of developing a DLT at the time of a new patient entry. Patients are evaluated for DLTs in the first 28 days of treatment. A noncompartmental analysis of PK of brigatinib is performed. The PK parameters are descriptively summarized with summary statistics. PK data additionally contribute to population PK analyses.

In addition to determination of the MTD, a descriptive summary of toxicities is reported.

Part A-2: Part A-2 of the study follows a Rolling-6 design. Two to 6 patients are accrued concurrently onto a dose level of brigatinib administered with the ALCL99 regimen. Decisions as to which dose level to enroll a patient are based on the number of patients experiencing DLTs, and the number of patients still at risk of developing a DLT at the time of a new patient entry. Patients are evaluated for DLTs in the first 28 days of treatment. A noncompartmental analysis of PK of brigatinib is performed. The PK parameters are descriptively summarized with summary statistics. PK data additionally contribute to population PK analyses.

In addition to determination of the MTD, a descriptive summary of toxicities is reported.

Part B, Cohort B-1: Cohort B-1 of the study uses confirmed ORR using RECIST v1.1 as the primary endpoint. All patients receiving at least 1 dose of brigatinib are analyzed. Twenty-eight patients provide approximately 90% power to rule out an uninteresting rate of 20% if the true response rate is 50% with a 1-sided alpha of 0.025. An interim analysis for futility is conducted on the first 14 patients enrolled in the study. If the conditional power to rule out an uninteresting rate of 20% is low, then the study may be closed for futility. PK data collected in this cohort contribute to population PK analyses.

Part B, Cohort B-2: Cohort B-2 of the study uses confirmed ORR using RECIST v1.1 as the primary endpoint and EFS at 2 years as a key secondary endpoint. Approximately 10 patients are enrolled in the study. PK data collected in this cohort contribute to population PK analyses.

D.4.3.2 Study 2: Randomized Phase 2 Study of Brigatinib in Combination with Dexamethasone, Ifosfamide, Methotrexate, Etoposide, and Cytarabine Followed by Brigatinib in Combination with Dexamethasone, Methotrexate, Cyclophosphamide and Doxorubicin (ALCL99 Regimen) Versus ALCL99 Regimen Alone in Previously Untreated Patients with High-Risk ALK+ ALCL Primary Objectives To assess the efficacy of brigatinib in combination with ALCL99 in patients ≥2 years with high-risk, previously untreated ALCL.

To assess the safety and tolerability of brigatinib in combination with ALCL99.

PK Objective

To collect plasma concentration-time data to contribute to population PK analyses.

Primary Endpoint

EFS at 2 years.

Secondary Endpoints

ORR, DOR, time to response, and OS.

Main Inclusion

Patients must be ≥2 years of age and <22 years of age.

Patients must have high-risk, ALK+ ALCL. −MDD+ at diagnosis AND antibody titer ≤1/750.

Patients are required to have an activating ALK aberration detected by certified assay (i.e., CLIA in the US) prior to screening. The report from this test is required to be submitted for eligibility. ALK immunohistochemistry can be used as a surrogate for FISH or NGS.

Patients must not be receiving other investigational medications within 30 days of study entry or while on study.

Patient must meet the organ function and system function requirements as stated in the protocol.

Main Exclusion

Patients with symptomatic CNS metastases that are neurologically unstable or require an increasing dose of corticosteroids.

Patients receiving strong or moderate CYP3A inhibitors or inducers within 14 days prior to the first dose of study drug.

Previously received an ALK inhibitor.

Patients have received any prior systemic chemotherapy for ALCL.

Sample Size

Approximately 104 patients ≥2 to <22 years of age are randomized in a 1:1 fashion to receive brigatinib in combination with ALCL99 or ALCL99 alone. (85 to 97 patients are ≤18 years of age.)

Duration of Follow-Up

Patients are followed for up to 3 years from randomization.

Treatments

Brigatinib is provided as oral solution or tablets for patients able to swallow oral dosage forms. The brigatinib+ ALCL99 treatment regimen used in Study 2 follow that explored in Part A-2 of Study 1.

Statistical Considerations:

Assuming a 2-sided alpha of 0.05, 2-year EFS of 24% in patients treated with ALCL99 alone, and 50% in patients treated with brigatinib in combination with ALCL99, the study requires 74 events observed to have 80% power at the final analysis. One interim analysis for futility is planned after the first 29 events have been observed. The trial is stopped for futility if the conditional power at the interim analysis is less than 20%. This power projection is based on a 2-sided log-rank test and is controlled at the 2-sided 0.05 level, adjusting for the proposed interim analysis plan. The number of events is fixed, but the enrollment number (N~104) may change based on an assessment of the overall event rate pooled across treatment groups (prior to the close of enrollment).

A tabular overview of all planned clinical studies is provided in the following table.

| Type of Study | Objectives Study Design Control | Treatments (Formulation, Route) | Treatments (Dose) | Study Population Number of Subjects Age Range | Key Endpoints |
|---|---|---|---|---|---|
| Study 1 | | | | | |
| Phase 1/2 | Safety, tolerability, PK, and preliminary efficacy Dose-escalation and expansion Uncontrolled | Brigatinib (oral solution in phase 1; oral solution or tablets in phase 2). ALCL99 (companion chemotherapy) | Brigatinib monotherapy (30 mg/m² to 100 mg/m²) Brigatinib (dose TBD) + standard doses of ALCL99. | Brigatinib monotherapy Dose-escalation: Advanced ALK + solid tumors or ALCL that failed prior SOC (N = 15, ≤18 years of age). ALCL expansion: relapsed/refractory ALCL (N = 15, ≤18 years of age). IMT expansion: unresectable/ recurrent IMT (N = 10, ≤18 years of age). Brigatinib + ALCL99 Newly diagnosed, high-risk ALCL (N = 12, ≤18 years of age) | RP2D of brigatinib monotherapy RP2D of brigatinib in combination with ALCL99 Pediatric PK parameters of brigatinib ORR |
| Study 2 | | | | | |
| Phase 2 | Efficacy and Safety Randomized Controlled | ALCL99, ALCL99 + brigatinib (oral solution or tablets based on ability to swallow). | Brigatinib (dose TBD) + Standard doses of ALCL99. | 85 to 97 patients 2 to 17 years of age with newly diagnosed, high-risk ALCL | EFS, ORR |

The embodiments described herein are intended to be merely exemplary, and those skilled in the art will recognize, or will be able to ascertain using no more than routine experimentation, numerous equivalents of specific compounds, materials, and procedures. All such equivalents are considered to be within the scope of the disclosure.

All of the patents, patent applications and publications referred to herein are incorporated herein in their entireties. Citation or identification of any reference in this application is not an admission that such reference is available as prior art to this application. The full scope of the disclosure is better understood with reference to the appended claims.

What is claimed is:

1. A method for treating a cancer in a pediatric patient having the cancer, comprising administering to the patient a therapeutically effective amount of Compound A of the formula:

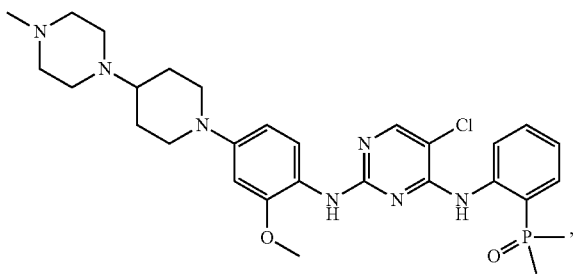

or a pharmaceutically acceptable salt thereof, wherein the cancer is inflammatory myofibroblastic tumor (IMT), anaplastic large cell lymphoma (ALCL), or neuroblastoma.

2. The method of claim 1, wherein the cancer is anaplastic lymphoma kinase positive (ALK+).

3. The method of claim 1 or 2, wherein the cancer is IMT or ALCL.

4. The method of claim 1 or 2, wherein the cancer is neuroblastoma.

5. The method of claim 1 or 2, wherein the cancer is IMT.

6. The method of claim 5, wherein the IMT is unresectable or recurrent IMT.

7. The method of claim 1 or 2, wherein the cancer is ALCL.

8. The method of claim 7, wherein the ALCL is relapsed or refractory ALCL.

9. The method of claim 7, wherein the ALCL is newly diagnosed ALCL.

10. The method of claim 9, wherein the ALCL is newly diagnosed ALCL with high risk for recurrence.

11. The method of claim 10, wherein the high risk for recurrence is characterized by minimal disseminated disease positive (MDD+) at diagnosis or anti-ALK antibody titer ≤1/750 at diagnosis.

12. The method of claim 1 or 2, wherein Compound A, or a pharmaceutically acceptable salt thereof, is administered orally.

13. The method of claim 12, wherein Compound A, or a pharmaceutically acceptable salt thereof, is administered once a day (QD).

14. The method of claim 13, wherein Compound A, or a pharmaceutically acceptable salt thereof, is administered at a dose of from about 30 mg/m² to about 100 mg/m².

15. The method of claim 14, wherein Compound A, or a pharmaceutically acceptable salt thereof, is administered at a dose of about 30, about 40, about 50, about 60, about 70, about 80, about 90, or about 100 mg/m².

16. The method of claim 1 or 2, further comprising administering to the patient a therapeutically effective amount of a one or more additional second therapeutic agents.

17. The method of claim 16, wherein the one or more additional therapeutic agents comprises cyclophosphamide, doxorubicin, vincristine, corticosteroid, ifosfamide, etoposide, methotrexate, or cytarabine, or a combination thereof.

18. The method of claim 17, wherein the corticosteroid is dexamethasone or hydrocortisone, or a combination thereof.

19. The method of claim 16, wherein the one or more additional therapeutic agents comprises dexamethasone, which is administered at a dose of from about 5 mg/m$^2$ to about 10 mg/m$^2$.

20. The method of claim 16, wherein the one or more additional therapeutic agents comprises cyclophosphamide, which is administered at a dose of about 200 mg/m$^2$.

21. The method of claim 16, wherein the one or more additional therapeutic agents comprises ifosfamide, which is administered at a dose of about 800 mg/m$^2$.

22. The method of claim 16, wherein the one or more additional therapeutic agents comprises methotrexate, which is administered at a dose of about 3 g/m$^2$.

23. The method of claim 16, wherein the one or more additional therapeutic agents comprises etoposide, which is administered at a dose of about 100 mg/m$^2$.

24. The method of claim 16, wherein the one or more additional therapeutic agents comprises cytarabine, which is administered at a dose of about 150 mg/m$^2$ and is administered twice a day.

25. The method of claim 16, wherein the one or more additional therapeutic agents comprises doxorubicin, which is administered at a dose of about 25 mg/m$^2$.

26. The method of claim 16, wherein Compound A, or a pharmaceutically acceptable salt thereof, and the one or more additional therapeutic agents are administered for one or more 21 days cycles.

27. The method of claim 26, wherein Compound A, or a pharmaceutically acceptable salt thereof, is administered on days 1-21 of the 21 days cycle.

28. The method of claim 27, wherein the one or more additional therapeutic agents comprises dexamethasone, which is administered on days 1-5 of the 21 days cycle.

29. The method of claim 27, wherein the one or more additional therapeutic agents comprises cyclophosphamide, which is administered on days 1 and 2 of the 21 day cycle.

30. The method of claim 27, wherein the one or more additional therapeutic agents comprises cyclophosphamide, which is administered on days 1-5 of the 21 day cycle.

31. The method of claim 27, wherein the one or more additional therapeutic agents comprises a combination of hydrocortisone, methotrexate, and cytarabine, which are administered on day 1 of the 21 days cycle.

32. The method of claim 27, wherein the one or more additional therapeutic agents comprises ifosfamide, which is administered on days 1-5 of the 21 days cycle.

33. The method of claim 27, wherein the one or more additional therapeutic agents comprises methotrexate, which is administered on day 1 of the 21 days cycle.

34. The method of claim 27, wherein the one or more additional therapeutic agents comprises etoposide, which is administered on days 4 and 5 of the 21 days cycle.

35. The method of claim 27, wherein the one or more additional therapeutic agents comprises cytarabine, which is administered on days 4 and 5 of the 21 days cycle.

36. The method of claim 27, wherein the one or more additional therapeutic agents comprises doxorubicin, which is administered on days 4 and 5 of the 21 days cycle.

* * * * *